US00PP21691P2

(12) United States Plant Patent
Jepsen

(10) Patent No.: US PP21,691 P2
(45) Date of Patent: Feb. 1, 2011

(54) *KALANCHOE* PLANT NAMED 'DESERT SURPRISE'

(50) Latin Name: *Kalanchoe humilis*
Varietal Denomination: Desert Surprise

(75) Inventor: Knud Jepsen, Hinnerup (DK)

(73) Assignee: Knud Depsen A/S, Hinnerup (DK)

( * ) Notice: Subject to any disclaimer, the term of this patent is extended or adjusted under 35 U.S.C. 154(b) by 0 days.

(21) Appl. No.: 12/583,683

(22) Filed: Aug. 25, 2009

(51) Int. Cl.
*A01H 5/00* (2006.01)

(52) U.S. Cl. ..... Plt./335

(58) Field of Classification Search ..... Plt./335
See application file for complete search history.

(56) References Cited

PUBLICATIONS

UPOV ROM GTITM Computer Database, GTI Jouve Retreival Software 2010/03 Citation for 'Desert Surprise'.*

* cited by examiner

*Primary Examiner*—Wendy C. Haas
(74) *Attorney, Agent, or Firm*—C. A. Whealy

(57) ABSTRACT

A new and distinct cultivar of *Kalanchoe* plant named 'Desert Surprise', characterized by its tall, upright, uniform and moderately vigorous growth habit; green and dark purple bi-colored leaves with undulate and crenate margins; freely flowering habit; small red purple-colored flowers; and excellent postproduction longevity.

3 Drawing Sheets

Botanical designation: *Kalanchoe humilis.*
Cultivar denomination: 'DESERT SURPRISE'.

BACKGROUND OF THE INVENTION

The present invention relates to a new and distinct cultivar of *Kalanchoe* plant, botanically known as *Kalanchoe humilis*, and hereinafter referred to by the name 'Desert Surprise'.

The new *Kalanchoe* plant is a product of a planned breeding program conducted by the Inventor in Hinnerup, Denmark. The objective of the breeding program is to create new *Kalanchoe* plants with unique and interesting foliage and flower forms and coloration.

The new *Kalanchoe* plant originated from a self-pollination made by the Inventor in Hinnerup, Denmark in January, 2008, of a proprietary selection of *Kalanchoe humilis* identified as code number 0077, not patented. The new *Kalanchoe* was discovered and selected by the Inventor as a flowering plant from within the progeny of the stated self-pollination in a controlled greenhouse environment in Hinnerup, Denmark on May 12, 2008.

Asexual reproduction of the new *Kalanchoe* plant by vegetative terminal cuttings in a controlled greenhouse environment in Hinnerup, Denmark since Jun. 9, 2008, has shown that the unique features of this new *Kalanchoe* plant are stable and reproduced true to type in successive generations.

SUMMARY OF THE INVENTION

Plants of the new *Kalanchoe* have not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Desert Surprise'. These characteristics in combination distinguish 'Desert Surprise' as a new and distinct cultivar of *Kalanchoe:*

1. Tall, upright, uniform and moderately vigorous growth habit.
2. Green and dark purple bi-colored leaves with undulate and crenate margins.
3. Freely flowering habit.
4. Small red purple-colored flowers.
5. Excellent postproduction longevity.

Plants of the new *Kalanchoe* can be compared to plants of the parent selection. Plants of the new *Kalanchoe* differ from plants of the parent selection primarily in plant uniformity.

Plants of the new *Kalanchoe* can be compared to plants of the proprietary selection of *Kalanchoe humilis* identified as code number KJ 2008 5043, not patented. In side-by-side comparisons conducted in Hinnerup, Denmark, plants of the new *Kalanchoe* differed from plants of the proprietary selection KJ 2008 5043 in the following characteristics:

1. Plants of the new *Kalanchoe* and the proprietary selection KJ 2008 5043 differed in leaf color as plants of the proprietary selection had less pronounced dark purple markings.
2. Plants of the new *Kalanchoe* and the proprietary selection KJ 2008 5043 differed in flower color as plants of the proprietary selection had white and dark purple-colored flowers.

BRIEF DESCRIPTION OF THE PHOTOGRAPHS

The accompanying colored photographs illustrate the overall appearance of the new *Kalanchoe* plant, showing the colors as true as it is reasonably possible to obtain in colored reproductions of this type. Colors in the photographs may differ slightly from the color values cited in the detailed botanical description which accurately describe the colors of the new *Kalanchoe* plant.

The photograph on the first sheet comprises a side perspective view of a typical flowering plant of 'Desert Surprise' grown in a container.

The photograph on the second sheet comprises a top perspective view of a typical flowering plant of 'Desert Surprise' grown in a container.

The photograph on the third sheet comprises close-up views of typical vegetative (bottom left) and generative (bottom right) leaves, a side perspective view of a typical inflorescence (top) and individual flowers (center) of 'Desert Surprise'.

DETAILED BOTANICAL DESCRIPTION

The aforementioned photographs and following observations, measurements and values describe plants grown in Hinnerup, Denmark in a glass-covered greenhouse during the winter and spring and under conditions which closely approximate commercial *Kalanchoe humilis* production. During the production of the plants, day temperatures averaged 19° C., night temperatures averaged 21° C. and light levels ranged from 10 kilolux to 50 kilolux. Unrooted cuttings were directly stuck in 10-cm containers and received long day/short night conditions (more than 14 hours of light) for about five weeks; plants then received photoinductive short day/long night conditions (minimum 14 hours darkness) until flowering. Plants were 25 weeks from planting when the photographs and the description were taken. In the detailed description, color references are made to The Royal Horticultural Society Colour Chart, 2001 Edition, except where general terms of ordinary dictionary significance are used.

Botanical classification: *Kalanchoe humilis* 'Desert Surprise'.

Parentage:

*Female, or seed, parent.*—Proprietary selection of *Kalanchoe humilis* identified as code number 0077, not patented.

*Male, or pollen, parent.*—Proprietary selection of *Kalanchoe humilis* identified as code number 0077, not patented.

Propagation:

*Type.*—By vegetative terminal cuttings.

*Time to initiate roots, summer.*—About two weeks at temperatures of 19° C. to 21° C.

*Time to initiate roots, winter.*—About three weeks at temperatures of 19° C. to 21° C.

*Time to produce a rooted young plant, summer.*—About three weeks at temperatures of 19° C. to 21° C.

*Time to produce a rooted young plant, winter.*—About 30 days at temperatures of 19° C. to 21° C.

*Root description.*—Fine to thick, fibrous; white in color.

*Rooting habit.*—Freely branching; moderately dense.

Plant description:

*Plant habit.*—Tall, upright, uniform and moderately vigorous growth habit; very freely flowering with numerous single flowers developing per plant; narrow inverted triangle; appropriate for 10-cm containers.

*Plant height at flowering.*—About 35 cm to 40 cm.

*Plant diameter at flowering.*—About 22 cm.

*Branching habit.*—About two to five lateral branches develop per plant.

Lateral branch description:

*Length.*—About 15 cm.

*Diameter.*—About 4 mm.

*Internode length.*—About 0.5 cm to 7 cm.

*Aspect.*—Erect.

*Strength.*—Strong.

*Texture.*—Smooth, glabrous.

*Color.*—Close to 191B.

Foliage description:

*Arrangement.*—Opposite, simple.

*Length, vegetative plants.*—About 4 cm to 11 cm.

*Width, vegetative plants.*—About 2 cm to 10 cm.

*Length, generative plants.*—About 3 cm to 11 cm.

*Width, generative plants.*—About 2 cm to 7 cm.

*Shape.*—Rotund to elliptical.

*Apex.*—Rounded to obtuse.

*Base.*—Rounded to cuneate.

*Margin.*—Undulate, crenate.

*Texture, upper and lower surfaces.*—Smooth, glabrous; leathery; succulent.

*Venation pattern.*—Pinnate.

*Color.*—Developing and fully expanded leaves, upper surface: Close to 138A; stripes, close to N186D; venation, close to 156D. Developing and fully expanded leaves, lower surface: Close to 138A; stripes, close to N186D; venation, close to 138A.

*Petioles.*—Length: About 5 mm to 10 mm. Diameter: About 5 mm to 6 mm. Texture, upper and lower surfaces: Smooth, glabrous. Color, upper and lower surfaces: Close to 138B.

Flower description:

*Flower arrangement and habit.*—Single tubular flowers arranged in dichasial cymes that arise from leaf axils; freely flowering habit with usually about 40 to 80 flowers per inflorescence.

*Fragrance.*—None detected.

*Natural flowering season.*—Plants of the new *Kalanchoe* flower from April to October when grown in an outdoor nursery; flower initiation and development can also be induced under artificial short day/long conditions (at least 14 hours of darkness) year-round in a greenhouse environment.

*Time to flower.*—Under short day/long night photoinductive conditions, about 84 days are required; actual time to flower is primarily dependent upon temperature and light intensity.

*Post-production longevity.*—Excellent post-production longevity; plants maintain good foliage and flower substance for about eight weeks under interior environmental conditions; individual flowers last about one week on the plant; flowers persistent.

*Inflorescence height.*—About 30 cm to 40 cm.

*Inflorescence diameter.*—About 5 cm to 9 cm.

*Flower diameter.*—About 3 mm.

*Flower length (height).*—About 8 mm.

*Flower bud.*—Shape: Oblong to lanceolate. Length: About 1.3 cm. Diameter: About 3 mm. Color: Towards the apex, close to N74C; center and base, close to 138A with stripes, close to 187A.

*Petals.*—Arrangement: About four in a single whorl fused at the base into a tubular shape. Length: About 4 mm. Width: About 2 mm. Shape: Roughly ovate. Apex: Acute. Margin: Entire. Texture, upper and lower surfaces: Smooth, glabrous. Color: When opening, upper and lower surfaces: Close to N74C. Fully opened, upper and lower surfaces: Close to N74C; stripes, close to 77B; color does not fade with development.

*Sepals.*—Appearance: Four fused at the base. Length: About 2 mm. Width: About 1 mm. Shape: Lanceolate. Apex: Acute. Base: Truncate. Margin: Entire. Texture, upper and lower surfaces: Smooth; glabrous. Color, immature, upper and lower surfaces: Close to 191A; stripes, close to N186D. Color, mature, upper and lower surfaces: Close to 191A; stripes, close to N186D.

*Peduncles.*—Length: About 15 cm to 25 cm. Diameter: About 2 mm to 8 mm. Aspect: About 45° from vertical. Strength: Strong. Texture: Smooth, glabrous; leathery. Color: Close to 191A; stripes, close to N186D.

*Pedicels.*—Length: About 2 mm to 5 mm. Diameter: About 0.5 mm to 1 mm. Aspect: Erect to about 45° from vertical. Strength: Strong. Texture: Smooth, glabrous; leathery. Color: Close to 191A; stripes, close to N186D.

*Reproductive organs.*—Androecium: Stamen number: About eight per flower. Anther shape: Rounded. Anther size: About 0.8 mm by 0.8 mm. Anther color: Close to 34B. Amount of pollen: Abundant. Pollen color: Close to 20B. Gynoecium: Pistil number: About eight per flower. Pistil length: About 1 mm. Style length: About 0.5 mm. Style color: Close to N146C. Stigma shape: Round. Stigma color: Close to 146C. Ovary color: Close to N186D.

*Seeds.*—Quantity per flower: About 40. Length: About 0.9 mm. Diameter: About 0.25 mm. Color, immature: Close to 145D. Color, mature: Close to 166A.

Temperature tolerance: Plants of the new *Kalanchoe* have been observed to tolerate temperatures from about 5° C. to about 30° C.

Pathogen/pest resistance: Plants of the new *Kalanchoe* have not been observed to be resistant to pests and pathogens common to *Kalanchoes.*

It is claimed:

1. A new and distinct *Kalanchoe* plant named 'Desert Surprise' as illustrated and described.

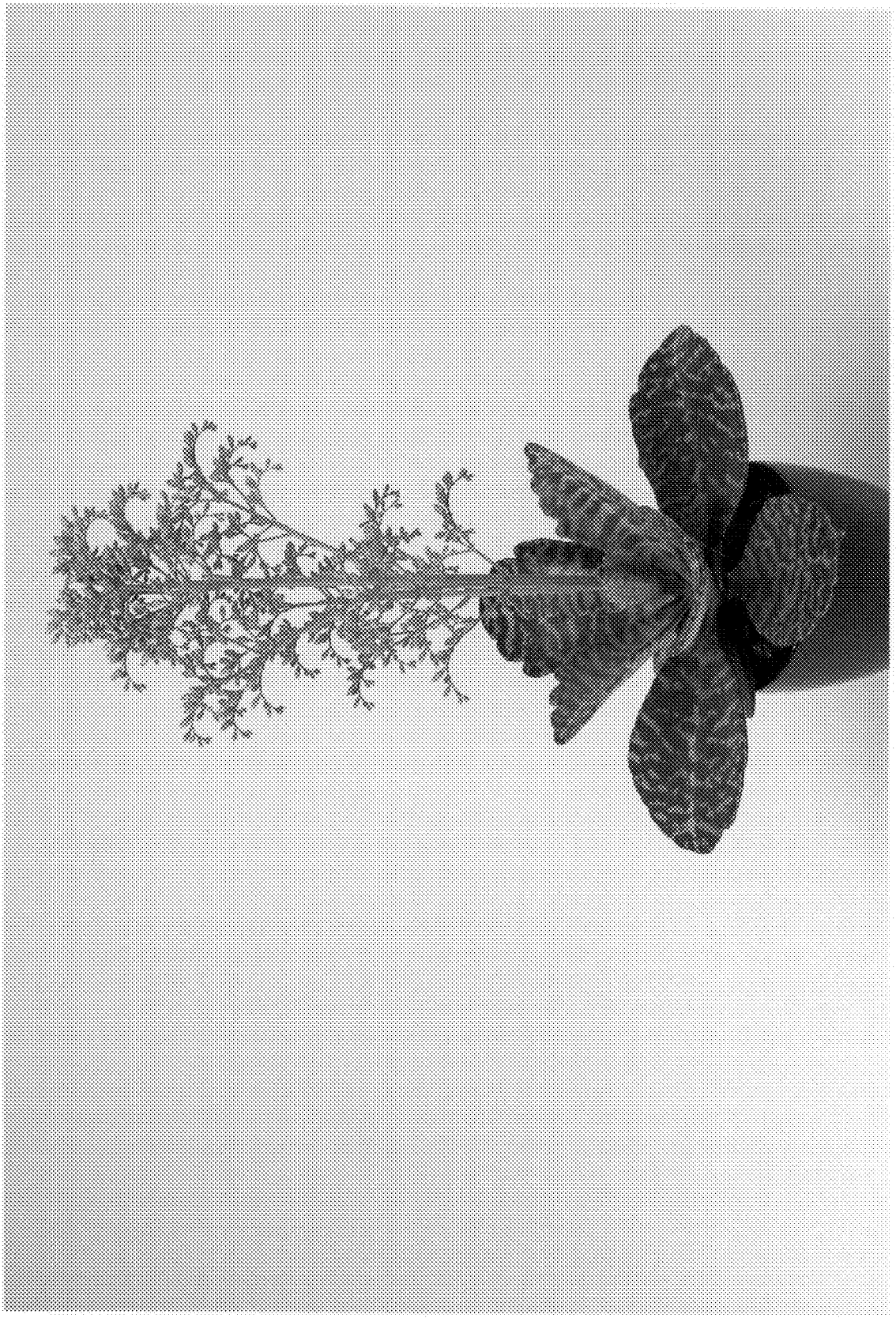

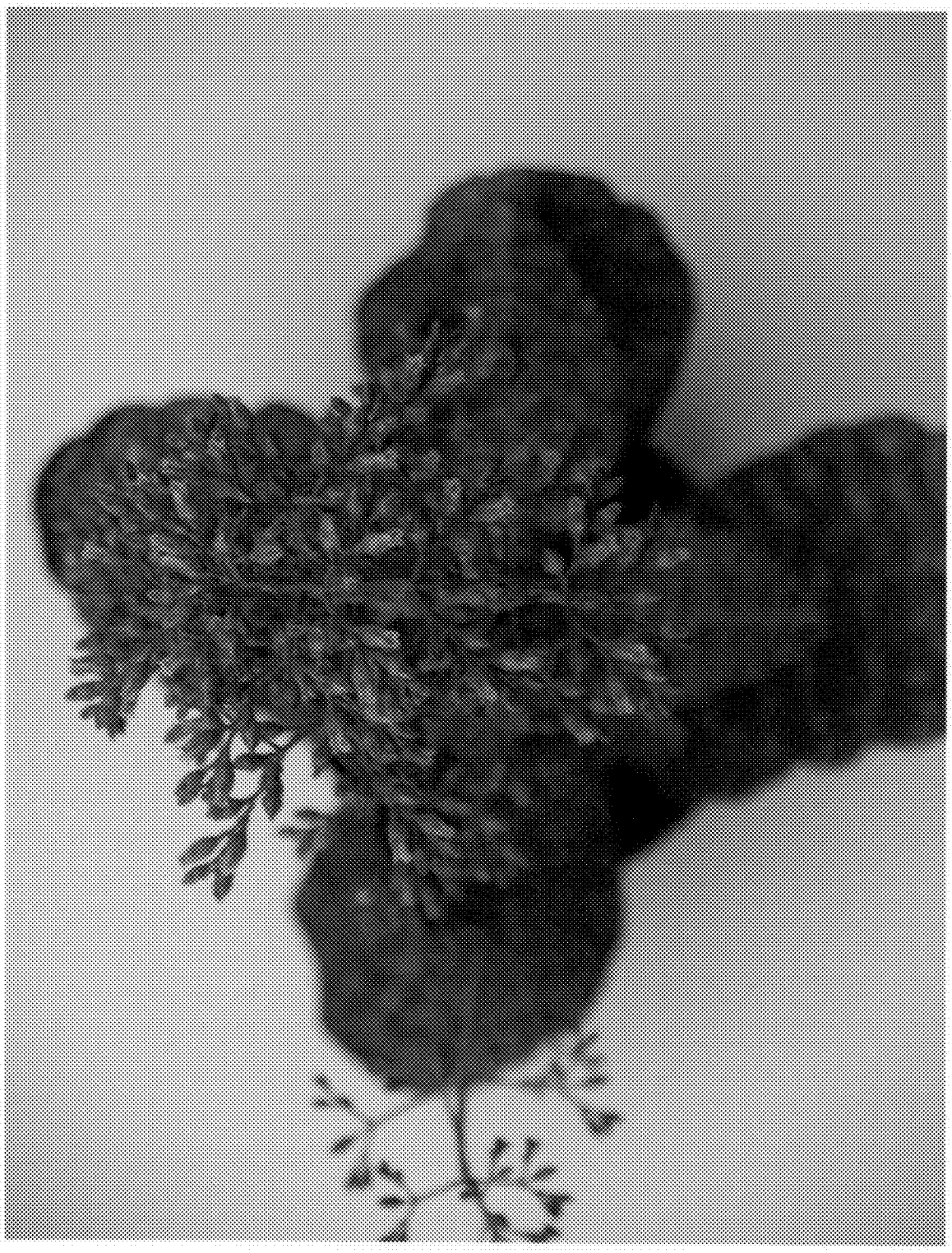

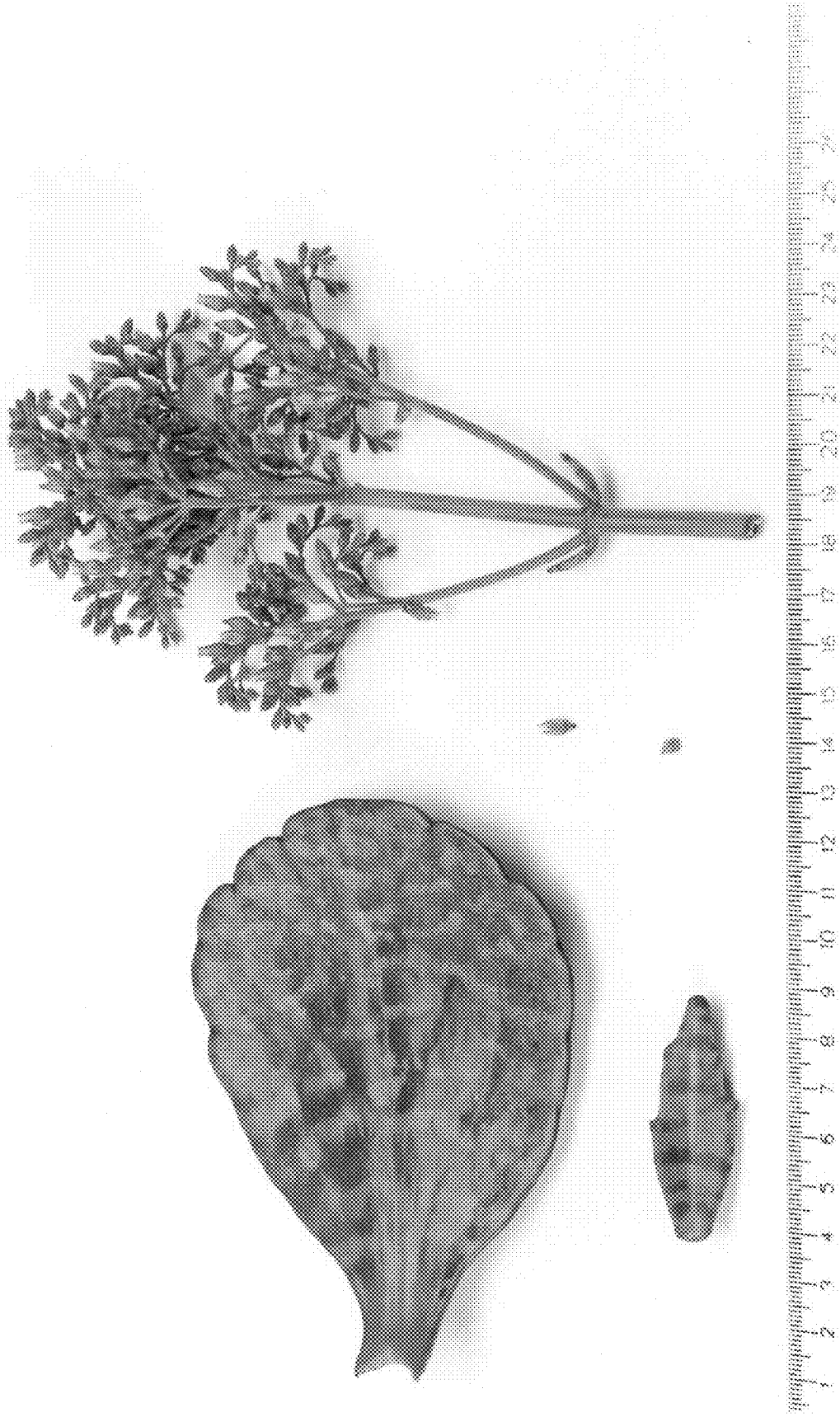

* * * * *